US00PP37237P2

(12) United States Plant Patent
Holtmaat

(10) Patent No.: US PP37,237 P2
(45) Date of Patent: Jan. 27, 2026

(54) ***RUDBECKIA* PLANT NAMED 'RUDBSS851'**

(50) Latin Name: *Rudbeckia hirta*
Varietal Denomination: RUDBSS851

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/232,228

(22) Filed: Jun. 9, 2025

(30) Foreign Application Priority Data

Oct. 15, 2024 (QZ) ..... PBR 2024394

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

(56) References Cited

U.S. PATENT DOCUMENTS

PP32,453 P2 * 11/2020 Holtmaat ..... A01H 5/02
Plt./289

* cited by examiner

*Primary Examiner* — Susan Mccormick Ewoldt
(74) *Attorney, Agent, or Firm* — Penny J. Aguirre

(57) ABSTRACT

A new cultivar of *Rudbeckia* plant named 'RUDBSS851' that is characterized by its ng and sturdy stems, its compact plant habit, its flowering that starts early in the season, its inflorescences with numerous ray florets covering the flower, disc florets are present but not visible as they are fully covered by the ray florets, its ray floret colors that are yellow-orange with the lower half greyed-purple and the tip tinged greyed-red, and its large flowers.

2 Drawing Sheets

Botanical classification: *Rudbeckia hirta.*
Variety denomination: 'RUDBSS851'.

CROSS-REFERENCE TO A RELATED APPLICATION

This application claims priority to European Community Plant Variety Office (CPVO) Plant Breeder's Rights Application No. 2024/2394 filed on Oct. 15, 2024, under 35 U.S.C. 119(f), the entire contents of which is incorporated by reference herein. This application is co-pending with a U.S. Plant Patent Applications filed for plants derived from the same breeding program that are entitled *Rudbeckia* Plant Named *Rudbeckia* Plant Named 'RUDBBCH767' (U.S. Plant patent application Ser. No. 19/232,149)*, *Rudbeckia* Plant Named 'RUDLPIR734' (U.S. Plant patent application Ser. No. 19/232,300)* and *Rudbeckia* Plant Named 'RUDBKST704' (U.S. Plant patent application Ser. No. 19/232,2186)*.

BACKGROUND OF THE INVENTION

The present invention relates to a new and distinct cultivar of *Rudbeckia hirta* and will hereafter by referred to by its cultivar name, 'RUDBSS851'. The new cultivar is an herbaceous perennial grown for use as a landscape plant.

'RUDBSS851' was selected in June of 2022 by the Inventor from amongst seedlings in a trial field in Zuidwolde, Netherlands. The trial field had been planted with seed derived from open pollination of numerous unpatented and unnamed proprietary plants from the Inventor's breeding program. The collected seeds were pooled before sowing and therefore the parentage is unknown.

Asexual propagation of the new cultivar was first accomplished under the direction of the Inventor by tissue culture using meristematic tissue in Heerhugowaard, The Netherlands in February of 2023. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBSS851' as a unique cultivar of *Rudbeckia.*

1. 'RUDBSS851' exhibits strong and sturdy stems.
2. 'RUDBSS851' exhibits a compact plant habit.
3. 'RUDBSS851' exhibits flowering that starts early in the season.
4. 'RUDBSS851' exhibits inflorescences with numerous ray florets covering the flower; disc florets are present but not visible as they are fully covered by the ray florets.
5. 'RUDBSS851' exhibits ray floret colors that are yellow-orange with the lower half greyed-purple and the tip tinged greyed-red.
6. 'RUDBSS851' exhibits large flowers.

'RUDBSS851' can be compared to the *Rudbeckia* cultivars 'RUDFA538' (U.S. Plant Pat. No. 32,453) and 'Rodeo Double Red' (not patented). 'RUDFA538' is similar to 'RUDBSS851' in having semi-double inflorescences. 'RUDHT53' differs from 'RUDBSS851' in having ray floret colors that are greyed-orange, lower ⅔rd greyed-purple and inflorescences that open 3 weeks later in the season. 'Rodeo Double Red' is similar to 'RUDBSS851' in having sturdy stems and a similar foliage color. 'Rodeo Double Red' differs from 'RUDBSS851' in having a taller plant height and inflorescences that open 3 weeks later in the season.

'RUDBSS851' can also be compared to the co-pending cultivars of *Rudbeckia*; 'RUDBBCH767', 'RUDLPIR734', and 'RUDBKST704'. 'RUDBBCH767' differs from 'RUDBSS851' in having only four whorls of ray florets that are golden yellow in color. 'RUDLPIR734' differs from 'RUDBSS851' in having a single row of ray florets that are bi-color. 'RUDBKST704' differs from 'RUDBSS851' in having a single row of ray florets that are yellow-orange with a lighter yellow-orange tips.

BRIEF DESCRIPTION OF THE DRAWINGS

The accompanying color photographs illustrate the overall appearance and distinct characteristics of the new *Rudbeckia*. The photographs were taken of a 4-month-old plant of 'RUDBSS851' as grown outdoors in a 23-cm container in Zuidwolde, The Netherlands.

The photograph in FIG. 1 is a side view of 'RUDBSS851' in bloom.

Figure 1:
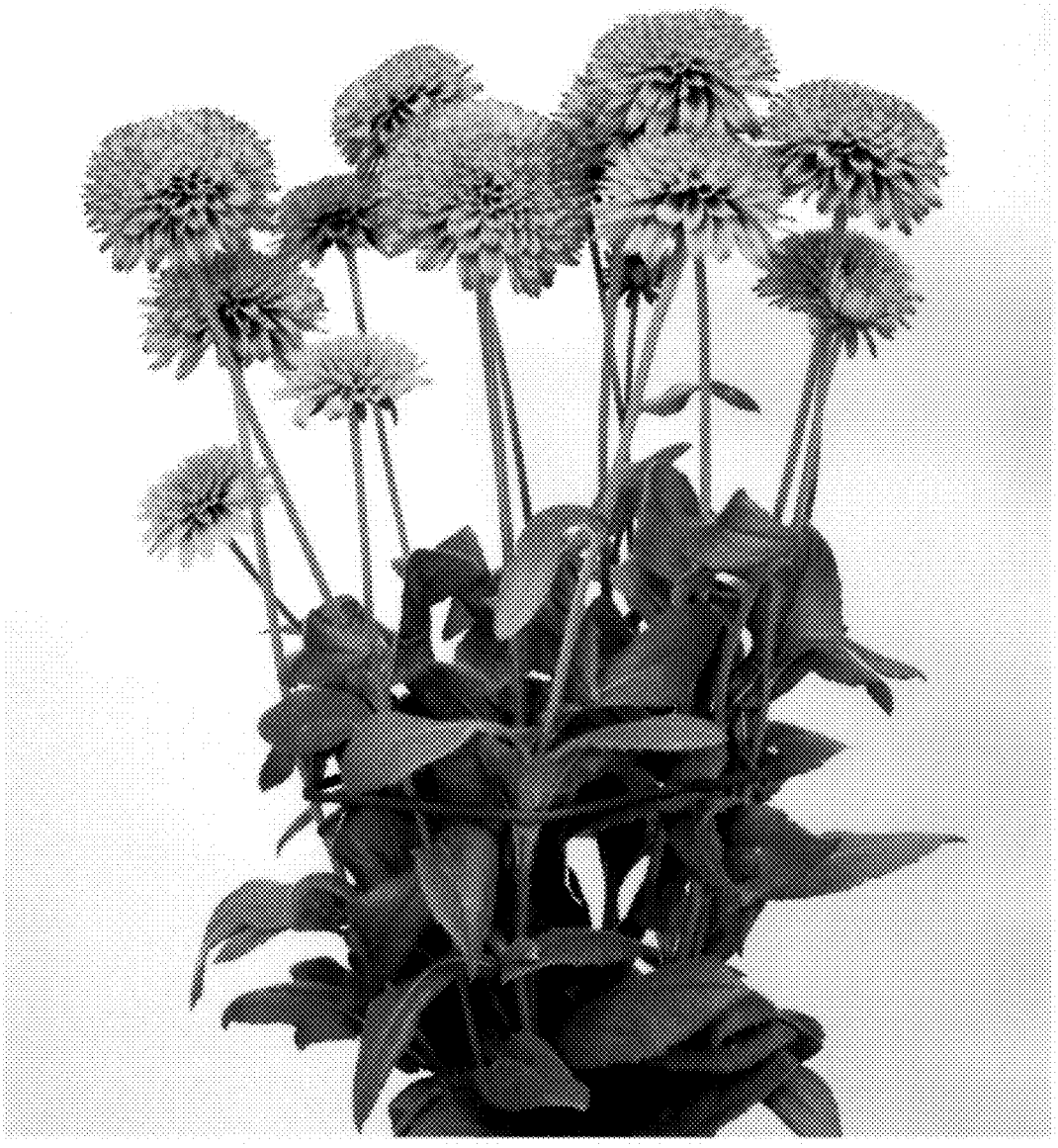
Figure 2:
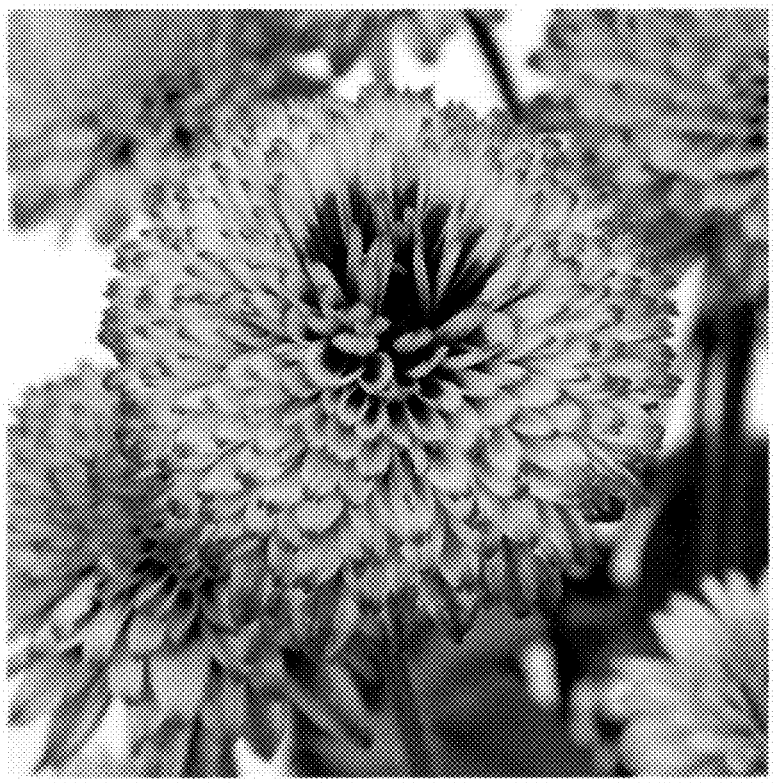

The photograph in FIG. 2 provides a close-up view of an inflorescence of 'RUDBSS851'.

Figure 3:
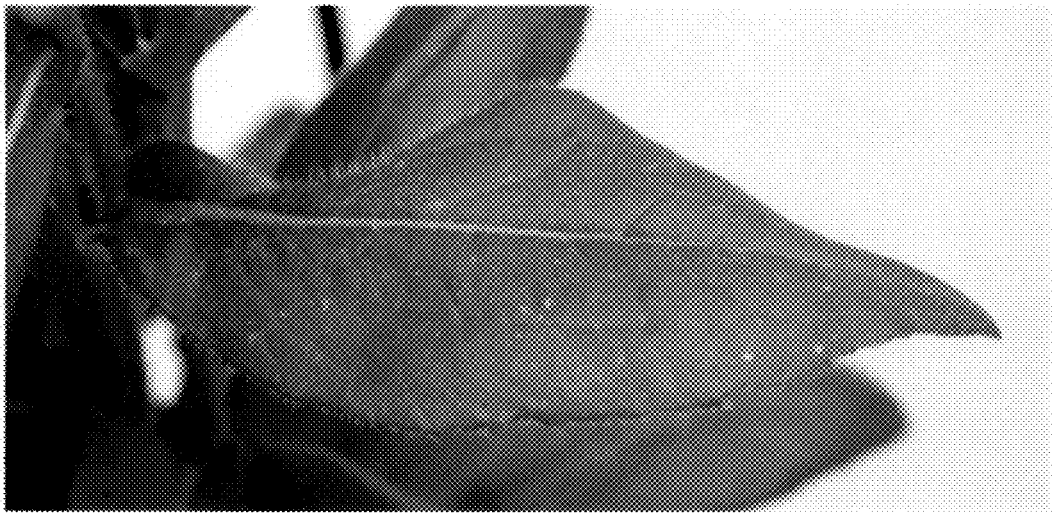

The photograph in FIG. 3 provides a close-up view of a leaf of 'RUDBSS851'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDBSS851' as grown outdoors in 23-cm containers in Zuidwolde, The Netherlands. The phenotype of the new cultivar may vary with variations in environmental, climatic, and cultural conditions, as it has not been tested under all possible environmental conditions. The color determination is in accordance with The 2015 (2019 reprint) Colour Chart of The Royal Horticultural Society, London, England, except where general color terms of ordinary dictionary significance are used.

General description:

*Blooming period*.—Early June to July in The Netherlands.

*Plant type*.—Perennial.

*Plant habit*.—Upright, compact.

*Plant shape*.—Vase-shaped.

*Height and spread*.—Average of 44 cm in height from soil level to top of foliar plane and 61 cm in height from soil level to top of floral plane, and 54 cm in diameter as a 4-month-old plant grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 2 weeks for root initiation with a young rooted plant produced in an average of 4 weeks.

*Growth rate and vigor*.—Highly vigorous.

Stem description:

*Shape*.—Very slightly angled, 5-sided.

*Stem color*.—Young stems; 144A, mature stems; 145A and 146B.

*Stem size*.—An average of 6 mm in diameter and an average of 23.9 cm in length.

*Stem surface*.—Moderately glossy and densely covered with strigose hairs an average of 2 mm in length and N155A in color.

*Stem number*.—Average of 8 main stems, 3 lateral branches per main stem.

*Internode length*.—An average of 4.5 cm in length.

*Stem aspect*.—Main stems; average of 20° to vertical, lateral branches; average of 20° to main stems.

*Branching*.—Freely branching from base with lateral stems.

Foliage description:

*Leaf shape*.—Obovate to elliptic obovate.

*Leaf division*.—Simple.

*Leaf base*.—Long cuneate.

*Leaf apex*.—Acute.

*Leaf venation*.—Pinnate, color upper surface 145B, color lower surface 146B.

*Leaf margins*.—Coarsely shallowly crenate-serrate, coarsely slightly undulate.

*Leaf attachment*.—Petiolate.

*Leaf arrangement*.—Alternate.

*Leaf size*.—Average of 13.8 cm in length and 5.5 cm in width.

*Leaf color*.—Young upper surface; 143A, young lower surface; 138A, mature upper surface; 137B, mature lower surface; 138B.

*Leaf surface*.—Upper surface matte, lower surface very slightly glossy, both surfaces rough to the touch, densely pubescent with short strigose hairs; an average of 1 mm in length and N155A in color.

*Petioles*.—Average of 4 mm in length, flattened, average diameter at widest point 8 mm and at narrowest point 4 mm, upper surface color 144B, lower surface color 144A, both surfaces slightly glossy and densely covered with strigose hairs; an average of 2 mm in length and N155A in color.

Flower description:

*Type*.—Terminal capitulum, consisting of ray florets and disc florets.

*Capitulum number*.—2 per stem, up to 16 per plant.

*Lastingness of inflorescence*.—Average of 2 weeks, persistent.

*Capitulum size*.—Matures to about 6.2 cm in height and 9.5 cm in diameter, disc size is an average of 2.6 cm in diameter.

*Fragrance*.—None.

*Involucral bracts* (*phyllaries*).—Cuneate base, bluntly acute apex, narrow oblong in shape, entire margins, average of 40 arranged in 4 rows, rotate, slightly curved downward in an angle of-40°, 1.9 cm in length and 6 mm in width, color; upper surface when fully open 143A, lower surface when fully open 146B, both surfaces very slightly glossy, all surfaces including margins are densely covered with strigose hairs; an average of 2 mm in length and N155A in color.

*Receptacle*.—Flattened globular in shape, an average of 9 mm in height, 1.8 cm in diameter, color; 157D, center 161A.

*Buds*.—Shape; flattened globular, immature ray florets pointed upward and slightly curled inwards, 2 cm in length, excluding and including involucral bracts 4.8 cm in width, color; immature ray florets 153D, base 152D, upper side of immature involucral bracts 143A, under side of immature involucral bracts 137C, surfaces are matte and densely covered with strigose hairs, on immature ray florets 0.5 mm in length and 4D in color, on involucral bracts 2 mm in length and N155A in color.

*Peduncle*.—Strong, straight on top of main flowering stem, average of 24.7 cm in length and 5 mm in diameter, color; 144C, angled 143A and 143B, surface moderately glossy and moderately covered with short strigose hairs; an average of 2 mm in length and N155A in color.

*Ray florets*.—Average of 550, rotate around the disc in 10 rows (whorls), narrow elliptic-oblong to oblanceolate in shape, average of 4.2 cm in length and 1.1 cm in width, emarginate to praemorse apex, cuneate base, entire margins, both surfaces are glabrous and moderately velvety, densely covered with very short hairs, 0.5 mm in length and 4D in color, held in various aspects, color; when opening upper surface 14A, tip 164A, lower 1/3rd strongly flushed with 183A to 183B, when opening lower surface 9B, lower 1/3rd 152D, when fully open upper surface 17B, tip 179A, lower half 187B, when fully open lower surface 12A, top 152C, and lower half 152C and 152D, veins 152B and 152C.

*Disc florets*.—Average of 950, 17 whorls arranged spirally on a conical receptacle, lower 80% fused into tube, tubular, upright, 1.1 cm in length and 4 mm in width, tubular, upper 20% free, free lobes have entire margins, apices of free lobes acute and curled backwards, both surfaces glabrous and slightly glossy, color; when opening upper and lower surface 200B, lower half 155C, when fully open upper and lower surface 200B, free lobes at the top 200A, lower half 155C, no spines, but a single bract is placed beside each disc floret; 1 per disc floret, flattened, an average of 7 mm in length and 1.5 mm in diameter, oblanceolate in shape, acute apex, narrowly cuneate base, color; apex N186C, mid-section 157C, narrowly margined N186C, base 157D, matte surface and moderately pubescent with hairs; an average of 0.2 mm in length, 150B in color.

Reproductive organs:

*Gynoecium*.—Pistil; 1, 7 mm in length, style; 4 mm in length, 157D in color, stigma; cleft, decurrent, 4 mm in diameter, a blend of N186C and 200A in color, ovary; 197C in color.

*Androecium*.—Stamens; 5, filaments; 2 mm in length, 155C in color, anther; narrow oblong in shape, 3 mm in length, 0.5 mm in width, N199A in color, pollen; low in quantity and 15A in color.

*Fruit/seed*.—None observed to date.

It is claimed:

1. A new and distinct cultivar of *Rudbeckia* plant named 'RUDBSS851' substantially as herein illustrated and described.

* * * * *